(12) United States Patent
Bonilla et al.

(10) Patent No.: US 12,325,883 B2
(45) Date of Patent: Jun. 10, 2025

(54) **LOOP-MEDIATED ISOTHERMAL AMPLIFICATION PRIMERS FOR SHIGA TOXIN-PRODUCING *E. COLI* (STEC) DETECTION**

(71) Applicant: NEOGEN FOOD SAFETY US HOLDCO CORPORATION, Lansing, MI (US)

(72) Inventors: Tonya D. Bonilla, Woodbury, MN (US); Neil Percy, St. Paul, MN (US); Christina A. Barnes, North Hudson, WI (US)

(73) Assignee: Neogen Food Safety US HoldCo Corporation, Lansing, MI (US)

( * ) Notice: Subject to any disclaimer, the term of this patent is extended or adjusted under 35 U.S.C. 154(b) by 1000 days.

(21) Appl. No.: 17/422,553

(22) PCT Filed: Jan. 9, 2020

(86) PCT No.: PCT/IB2020/050153
§ 371 (c)(1),
(2) Date: Jul. 13, 2021

(87) PCT Pub. No.: WO2020/148610
PCT Pub. Date: Jul. 23, 2020

(65) Prior Publication Data
US 2023/0183819 A1 Jun. 15, 2023

Related U.S. Application Data

(60) Provisional application No. 62/847,456, filed on May 14, 2019, provisional application No. 62/792,670, filed on Jan. 15, 2019.

(51) Int. Cl.
*C12Q 1/689* (2018.01)
*C12Q 1/6844* (2018.01)

(52) U.S. Cl.
CPC .......... *C12Q 1/689* (2013.01); *C12Q 1/6844* (2013.01); *C12Q 2600/16* (2013.01)

(58) Field of Classification Search
CPC ... C12Q 1/689; C12Q 1/6844; C12Q 2600/16
See application file for complete search history.

(56) References Cited

U.S. PATENT DOCUMENTS 7,371,545 B2  5/2008  Tisi
8,309,308 B2  11/2012  Tisi

FOREIGN PATENT DOCUMENTS

| CN | 101487057 | 7/2009 |
| KR | 2015-0143347 | 12/2015 |
| WO | WO 2000-028082 | 5/2000 |
| WO | WO 2001-034790 | 5/2001 |
| WO | WO 2001-077317 | 10/2001 |
| WO | WO 2002-024902 | 3/2002 |
| WO | WO 2018-017880 | 1/2018 |

OTHER PUBLICATIONS

Zhao, X et al Development and application of a loop-mediated isothermal amplification method on rapid detection *E. coli* 0157 strains from food samples 2010 Mol Biol Rep 37:2183-2188 (Year: 2010).*
Wong, Y-P et al. Loop-mediated isothermal amplification (LAMP): a versatile technique for detection of micro-organisms. 2017. Jour Appl Micb 12:626-643. (Year: 2017).*
Bai et al, Identification and pathogenomic analysis of an *Escherchia coli* strain producing a novel Shiga toxin 2 subtype, 2018, Sci Reports, 8:6756. (Year: 2018).*
Wang et al, Loop-mediated isothermal amplification assays for detecting shiga toxin-producing *Escherechia coli* in ground beef and human stools, 2013, Jour Clin Mich, 50, 91-97. (Year: 2012).*
Dong, "Development of a multiplex loop-mediated isothermal amplification assay to detect shiga toxin-producing *Escherichia coli* in cattle", Jun. 2014, Journal of Veterinary Science, vol. 15, No. 2, pp. 317-325.
Kouguchi, "Homogenous, real-time duplex loop-mediated isothermal amplification using a single fluorophore-labeled primer and an intercalator dye: Its application to the simultaneous detection of Shiga toxin genes 1 and 2 in Shiga toxigenic *Escherichia coli* isolates", Aug. 2010, Molecular and Cellular Probes, vol. 24, No. 4, pp. 190-195.
Penzel, "Rapid culture-based identification of Shiga toxin-producing *Escherichia coli* and *Shigella* spp./Enteroinvasive *E. coli* using the eazyplex® EHEC complete assay", European Journal of Clinical Microbiology & Infectious Diseases, Sep. 2019, vol. 39, No. 1, pp. 151-158.
"Primer and Probe Sequences and Reagent Concentrations for non-O157 Shiga Toxin-Producing *Escherichia coli* (STEC) Real-Time PCR Assay", Feb. 2019, Microbiology Laboratory Guidebook Method 5C—Appendix 4.00, United States Department of Agriculture Foods Safety and Inspection Service, pp. 1-8.
Zhao, "Development and application of a loop-mediated isothermal amplification method on rapid detection *Escherichia coli* O157 strains from food samples", Molecular Biology Reports, Aug. 2009, vol. 37, No. 5, pp. 2183-2188.
International Search Report for PCT International Application No. PCT/IB2020/050153, mailed on Jun. 23, 2020, 10 pages.

* cited by examiner

*Primary Examiner* — Samuel C Woolwine
*Assistant Examiner* — Lisa Horth
(74) *Attorney, Agent, or Firm* — HYLTON-RODIC LAW PLLC

(57) ABSTRACT

Primers and methods of amplifying DNA from shiga toxins stx1 and stx2 designed for use in a multiplex method and useful in detecting shiga-toxin producing *E. Coli* (STEC). The primers being especially designed for use in Loop-mediated Isothermal Amplification (LAMP).

12 Claims, No Drawings
Specification includes a Sequence Listing.

LOOP-MEDIATED ISOTHERMAL AMPLIFICATION PRIMERS FOR SHIGA TOXIN-PRODUCING *E. COLI* (STEC) DETECTION

CROSS REFERENCE TO RELATED APPLICATIONS

This application is a national stage filing under 35 U.S.C. 371 of PCT/IB2020/050153, filed 9 Jan. 2020, which claims the benefit of U.S. Provisional Application No. 62/792,670, filed 15 Jan. 2019, and U.S. Provisional Application No. 62/847,456, filed 14 May 2019, the disclosures of which are incorporated by reference in their entireties herein.

SEQUENCE LISTING

This application contains a Sequence Listing electronically submitted via EFS-Web to the United States Patent and Trademark Office as an ASCII text filed entitled "2021-01-18-81683US006-Sequence_Listing_ST25.txt" having a size of 2.20 kilobytes and created on 18 Jan. 2022, which is substantially identical (except for formal matters) to a Sequence Listing that was electronically submitted via ePCT to the International Bureau with PCT/IB2020/050153. The information contained in the Sequence Listing is incorporated by reference herein.

BACKGROUND

Shiga toxin-producing *Escherichia coli* (*E. coli*), sometimes known as STEC, are characterized by the production of Shiga toxin and intimin adhesins. These strains of *E. coli* contain genes encoding Shiga toxin-stx1 or stx2 and intimin adhesin-eae. There is a subgroup of STEC, often referred to as enterohemorrhagic *E. coli* or EHEC, that is capable of causing hemolytic uremic syndrome or HUS.

Loop-mediated isothermal amplification (LAMP) is a method of amplifying DNA that has been described, for example, in WO0028082, WO0134790, and WO0177317.

SUMMARY

A primer set can include a primer selected from the group consisting of a primer having at least 80% homology, at least 85% homology, optionally at least 90% homology, optionally at least 95% homology, optionally at least 99% homology, or optionally being identical to SEQ ID NO: 3; or a primer having at least 80% homology, optionally at least 85% homology, optionally at least 90% homology, optionally at least 95% homology, optionally at least 99% homology, or optionally being identical to SEQ ID NO: 6, or a combination of the foregoing primers.

A lyophilized pellet or powder can include a primer set as disclosed herein.

A method of amplifying target DNA comprising exposing the target DNA to a primer set or lyophilized pellet or powder as disclosed herein under conditions that are suitable for amplification of the target DNA is disclosed.

DETAILED DESCRIPTION

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Some terms in this disclosure are defined below. Other terms will be familiar to the person of skill in the art and should be afforded the meaning that a person of ordinary skill in the art would have ascribed to them.

The terms "common," "typical," and "usual," as well as "commonly," "typically," and "usually" are used herein to refer to features that are often employed in the invention and, unless specifically used with reference to the prior art, are not intended to mean that the features are present in the prior art, much less that those features are common, usual, or typical in the prior art.

The term "LAMP" is an acronym for loop-mediated isothermal amplification, a method of amplifying DNA that has been described, for example, in WO0028082, WO0134790, and WO0177317.

Detection of microorganisms can be accomplished by amplifying a segment of DNA that is specific to the type of microorganism to be detected followed by detection of the amplified DNA. If the DNA is present at detectable levels after amplification, this indicates the presence of the microorganism of interest. If no DNA is present, this indicates that the DNA of interest, and thus the microorganism of interest, was not present. PCR is one well-recognized way to amplify DNA that relies on thermocycling. LAMP is another method for amplifying DNA. Unlike PCR, LAMP takes place at a constant elevated temperature, typically about 60° C., such as 50° C. to 70° C., thus eliminating the need for thermocycling.

Briefly, LAMP requires four different primers, although frequently six primers are used. The required primers are two lamp primers and two displacement primers. The optional primers are two loop primers. The lamp primers have a 3' segment that binds to a specific target sequence and a 5' segment that is the reverse compliment to an internal target sequence. Extension from a displacement primer generates a primary amplicon and formation of a self-priming loop structure. The loop primers, which are optional, bind within the loop structures to facilitate exponential amplification. A primer set for amplification contains two lamp primers (known as LampF and LampB), two displacement primers (known as DisF and DisB), and optionally one or two loop primers (known as LoopF and LoopB).

Of the primers in each primer set, at least the two lamp primers do not exist in nature. This is because one end of each lamp primer is complementary to a segment of DNA on the forward strand of the template, and the other end of each lamp primer is complementary to a non-contiguous segment of DNA on the reverse strand of the template. Further, at least the 5' primer or primer segment of each lamp primer is a reverse complement of the target DNA, which also does not exist in nature.

Once amplified, the DNA can be detected by a variety of methods, including the bioluminescence in real time (BART) method. The 3M Molecular Detection System (available from 3M Company, St. Paul, MN, USA) is a commercially available system that uses BART to detect microorganisms after the portion of DNA of the microorganisms is amplified with LAMP.

A problem is that there are no known primers that can be used for LAMP amplification of stx1 or stx2 gene DNA. Another problem is that STEC bacterial are not currently detectable by way of LAMP amplification followed by a detection method. Another problem is how to amplify both stx1 and stx2 simultaneously, and thereby be able to detect in one trial the presence of either stx1 or stx2.

This disclosure provides primers that are useable for amplification of stx1 by LAMP methodology. This disclosure also provides primers that are useable for amplification of stx2 by LAMP methodology. The primer sets for detecting stx1 and stx2 may be combined into a single primer set which detects both stx1 and stx2; this particular approach is most common because in most cases it is not necessary to differentiate whether the STEC contains the stx1 gene, the stx2 gene, or both.

A primer set for stx1 can include a lamp primer, particularly the stx1 all var LampF primer having the sequence of SEQ ID NO: 3. Optionally, the stx1 all var LampF primer can have a sequence that has at least 99% homology, at least 95% homology, at least 90% homology, at least 85% homology, or at least 80% homology to SEQ ID NO: 3.

Any suitable displacement primer for stx1 can be used in the primer set along with the aforementioned lamp primer. One suitable displacement primer is the stx1 all var DisF primer having the sequence of SEQ ID NO: 1. Optionally, the stx1 all var DisF primer can have a sequence that has at least 99% homology, at least 95% homology, at least 90% homology, at least 85% homology, or at least 80% homology to SEQ ID NO: 1. In principle other displacement primers could be used.

A primer set for stx1 can optionally include a suitable loop primer. One suitable loop primer is the stx1 all var LoopF primer having the sequence of SEQ ID NO: 2. Optionally, the stx1 all var LoopF primer can have a sequence that has at least 99% homology, at least 95% homology, at least 90% homology, at least 85% homology, or at least 80% homology to SEQ ID NO: 2. In principle, other loop primers could be used.

A primer set for stx1 can include, typically in addition to but in some cases as an alternative, to the stx1 all var LampF primer discussed above, the stx1 all var LampB primer having the sequence of SEQ ID NO: 6. Optionally, the stx1 all var LampB primer can have a sequence that has at least 99% homology, at least 95% homology, at least 90% homology, at least 85% homology, or at least 80% homology to SEQ ID NO: 6.

Any suitable displacement primer for stx1 can be used in the primer set along with the aforementioned lamp primer. One suitable displacement primer is the stx1 all var DisB primer having the sequence of SEQ ID NO: 4. Optionally, the stx1 all var DisB primer can have a sequence that has at least 99% homology, at least 95% homology, at least 90% homology, at least 85% homology, or at least 80% homology to SEQ ID NO: 4. In principle, other displacement primers could be used.

A primer set for stx1 can optionally include a suitable loop primer. One suitable loop primer is the stx1 all var LoopB primer having the sequence of SEQ ID NO: 5. Optionally, the stx1 all var LoopB primer can have a sequence that has at least 99% homology, at least 95% homology, at least 90% homology, at least 85% homology, or at least 80% homology to SEQ ID NO: 5. In principle, other loop primers could be used.

A primer set for stx2 can include a lamp primer for stx2 such as the stx2 all var LampF primer having the sequence of SEQ ID NO: 9. Optionally, the stx1 all var LampF primer can have a sequence that has at least 99% homology, at least 95% homology, at least 90% homology, at least 85% homology, or at least 80% homology to SEQ ID NO: 9.

Any suitable displacement primer for stx2 can be used in the primer set along with the aforementioned lamp primer. One suitable displacement primer is the stx2 all var DisF primer having the sequence of SEQ ID NO: 7. Optionally, the stx1 all var DisF primer can have a sequence that has at least 99% homology, at least 95% homology, at least 90% homology, at least 85% homology, or at least 80% homology to SEQ ID NO: 7.

A primer set for stx2 can optionally include a suitable loop primer. One suitable loop primer is the stx2 all var LoopF primer having the sequence of SEQ ID NO: 8. Optionally, the stx2 all var LoopF primer can have a sequence that has at least 99% homology, at least 95% homology, at least 90% homology, at least 85% homology, or at least 80% homology to SEQ ID NO: 8.

A primer set for stx2 can include, in addition to or in the alternative to the lamp primer stx2 all var LampF, discussed above, a lamp primer for stx2 such as the stx2 all var LampB primer having the sequence of SEQ ID NO: 12. Optionally, the stx2 all var LampB primer can have a sequence that has at least 99% homology, at least 95% homology, at least 90% homology, at least 85% homology, or at least 80% homology to SEQ ID NO: 12.

Any suitable displacement primer for stx2 can be used in the primer set along with the aforementioned lamp primer. One suitable displacement primer is the stx2 all var DisB primer having the sequence of SEQ ID NO: 10. Optionally, the stx2 all var DisB primer can have a sequence that has at least 99% homology, at least 95% homology, at least 90% homology, at least 85% homology, or at least 80% homology to SEQ ID NO: 10.

A primer set for stx2 can optionally include a suitable loop primer. One suitable loop primer is the stx2 all var LoopB primer having the sequence of SEQ ID NO: 11. Optionally, the stx2 all var LoopB primer can have a sequence that has at least 99% homology, at least 95% homology, at least 90% homology, at least 85% homology, or at least 80% homology to SEQ ID NO: 11.

Any primer set as described herein can be in the form of a lyophilized pellet or powder, which can optionally contain other materials. Examples of other materials that can be included in the lyophilized pellet or powder include sugars, such as glucose, lyophilization aids, preservatives, antioxidants, and the like.

EMBODIMENTS

A list of illustrative embodiments appears below. These embodiments are not meant to be limiting; other embodiments are also possible.

1. A primer set comprising a primer having at least 80% homology to SEQ ID NO: 3.

1a. A primer set of embodiment 1, comprising a primer having at least 85% homology to SEQ ID NO: 3.

1b. A primer set of embodiment 1, comprising a primer having at least 90% homology to SEQ ID NO: 3.

1c. A primer set of embodiment 1, comprising a primer having at least 95% homology to SEQ ID NO: 3

1d. A primer set of embodiment 1, comprising a primer having at least 99% homology to SEQ ID NO: 3.

1e. A primer set of embodiment 1, comprising a primer of SEQ ID NO: 3.

2. The primer set of any of the preceding embodiments, further comprising a primer having at least 80% homology to SEQ ID NO. 1.

2a. A primer set of embodiment 1, comprising a primer having at least 85% homology to SEQ ID NO: 1.

2b. A primer set of embodiment 1, comprising a primer having at least 90% homology to SEQ ID NO: 1.

2c. A primer set of embodiment 1, comprising a primer having at least 95% homology to SEQ ID NO: 1.

2d. A primer set of embodiment 1, comprising a primer having at least 99% homology to SEQ ID NO: 1.

2e. A primer set of embodiment 1, comprising a primer of SEQ ID NO: 1.

3. The primer set of any of the preceding claims, further comprising a primer having at least 80% homology to SEQ ID NO. 2.

3a. A primer set of embodiment 1, comprising a primer having at least 85% homology to SEQ ID NO: 2.

3b. A primer set of embodiment 1, comprising a primer having at least 90% homology to SEQ ID NO: 2.

3c. A primer set of embodiment 1, comprising a primer having at least 95% homology to SEQ ID NO: 2.

3d. A primer set of embodiment 1, comprising a primer having at least 99% homology to SEQ ID NO: 2.

3e. A primer set of embodiment 1, comprising a primer of SEQ ID NO: 2.

4. A primer set comprising a primer having at least 80% homology to SEQ ID NO: 6.

4a. A primer set of embodiment 4, comprising a primer having at least 85% homology to SEQ ID NO: 6.

4b. A primer set of embodiment 4, comprising a primer having at least 90% homology to SEQ ID NO: 6.

4c. A primer set of embodiment 4, comprising a primer having at least 95% homology to SEQ ID NO: 6.

4d. A primer set of embodiment 4, comprising a primer having at least 99% homology to SEQ ID NO: 6.

4e. A primer set of embodiment 4, comprising a primer of SEQ ID NO: 6.

5. The primer set of embodiment 4, further comprising a primer having at least 80% homology to SEQ ID NO: 4.

5a. The primer set of embodiment 5, comprising a primer having at least 85% homology to SEQ ID NO: 4.

5b. The primer set of embodiment 5, comprising a primer having at least 85% homology to SEQ ID NO: 4.

5c. The primer set of embodiment 5, comprising a primer having at least 90% homology to SEQ ID NO: 4.

5d. The primer set of embodiment 5, comprising a primer having at least 95% homology to SEQ ID NO: 4.

5e. The primer set of embodiment 5, comprising a primer having at least 99% homology to SEQ ID NO: 4.

6. The primer set of any of embodiments 4-5e, further comprising a primer of SEQ ID NO: 5.

7. A primer set comprising a primer having at least 80% homology to SEQ ID NO: 9.

7a. The primer set of embodiment 7 comprising a primer having at least 85% homology to SEQ ID NO: 9.

7b. The primer set of embodiment 7 comprising a primer having at least 90% homology to SEQ ID NO: 9.

7c. The primer set of embodiment 7 comprising a primer having at least 95% homology to SEQ ID NO: 9.

7d. The primer set of embodiment 7 comprising a primer having at least 99% homology to SEQ ID NO: 9.

7e. The primer set of embodiment 7 comprising a primer of SEQ ID NO: 9

8. The primer set of any of embodiments 7-7e, further comprising a primer having at least 80% homology to SEQ ID NO: 7.

8a. The primer set of embodiment 8 comprising a primer having at least 85% homology to SEQ ID NO: 7.

8b. The primer set of embodiment 8 comprising a primer having at least 90% homology to SEQ ID NO: 7.

8c. The primer set of embodiment 8 comprising a primer having at least 95% homology to SEQ ID NO: 7.

8d. The primer set of embodiment 8 comprising a primer having at least 99% homology to SEQ ID NO: 7.

8e. The primer set of embodiment 8 comprising a primer of SEQ ID NO: 7.

9. The primer set of any of embodiments 7-8e, further comprising a primer having at least 80% homology to SEQ ID NO: 8.

9a. The primer set of embodiment 9, comprising a primer having at least 85% homology to SEQ ID NO: 8.

9b. The primer set of embodiment 9, comprising a primer having at least 90% homology to SEQ ID NO: 8.

9c. The primer set of embodiment 9, comprising a primer having at least 90% homology to SEQ ID NO: 8.

9d. The primer set of embodiment 9, comprising a primer having at least 99% homology to SEQ ID NO: 8.

9e. The primer set of embodiment 9, comprising a primer of SEQ ID NO: 8.

10. A primer set comprising a primer having at least 80% homology to SEQ ID NO: 12.

10a. The primer set of embodiment 10, comprising a primer having at least 85% homology to SEQ ID NO: 12.

10b. The primer set of embodiment 10, comprising a primer having at least 90% homology to SEQ ID NO: 12.

10c. The primer set of embodiment 10, comprising a primer having at least 90% homology to SEQ ID NO: 12.

10d. The primer set of embodiment 10, comprising a primer having at least 99% homology to SEQ ID NO: 12.

10e. The primer set of embodiment 10, comprising a primer of SEQ ID NO: 12.

11. The primer set of claim 10, further comprising a primer having at least 80% homology to SEQ ID NO: 10.

11a. The primer set of embodiment 11, comprising a primer having at least 85% homology to SEQ ID NO: 10.

11b. The primer set of embodiment 11, comprising a primer having at least 90% homology to SEQ ID NO: 10.

11c. The primer set of embodiment 11, comprising a primer having at least 90% homology to SEQ ID NO: 10.

11d. The primer set of embodiment 11, comprising a primer having at least 99% homology to SEQ ID NO: 10.

11e. The primer set of embodiment 11, comprising a primer of SEQ ID NO: 10.

12. The primer set of any of claims 10-11, further comprising a primer having at least 80% homology to SEQ ID NO: 11.

12a. The primer set of embodiment 12, comprising a primer having at least 85% homology to SEQ ID NO: 11.

12b. The primer set of embodiment 12, comprising a primer having at least 90% homology to SEQ ID NO: 11.

12c. The primer set of embodiment 12, comprising a primer having at least 90% homology to SEQ ID NO: 11.

12d. The primer set of embodiment 12, comprising a primer having at least 99% homology to SEQ ID NO: 11.

12e. The primer set of embodiment 12, comprising a primer of SEQ ID NO: 11.

13. A method of amplifying target DNA comprising exposing the target DNA to a primer set of any of the preceding claims under conditions that are suitable for amplification of the target DNA.

14. The method of claim 13, wherein the conditions include a temperature of 50° C. to 70° C.

15. The method of any of claims 13-14, further comprising detecting the presence of amplified target DNA.

16. A primer set comprising a primer selected from the group consisting of a primer having at least 80% homology, at least 85% homology, optionally at least 90% homology, optionally at least 95% homology, optionally at least 99% homology, or optionally being identical to SEQ ID NO: 3, a primer having at least 80% homology, optionally at least 85% homology, optionally at least 90% homology, optionally at least 95% homology, optionally at least 99% homology, or optionally being identical to SEQ ID NO: 5, or a combination of the foregoing primers.

17. A primer set of embodiment 16, comprising a primer having at least 80% homology to SEQ ID NO: 3 and primer having at least 80% homology, optionally at least 85% homology, optionally at least 90% homology, optionally at least 95% homology, optionally at least 99% homology, optionally being identical to SEQ ID NO: 5.

18. The primer set of any of embodiments 16-17, further comprising a primer having at least 80% homology, optionally at least 85% homology, optionally at least 90% homology, optionally at least 95% homology, optionally at least 99% homology, optionally being identical to SEQ ID NO. 1

19. The primer set of any of embodiments 16-18, further comprising a primer having at least 80% homology, optionally at least 85% homology, optionally at least 90% homology, optionally at least 95% homology, optionally at least 99% homology, optionally being identical to SEQ ID NO. 2.

20. The primer set of any of embodiments 16-19, further comprising a primer having at least 80% homology, optionally at least 85% homology, optionally at least 90% homology, optionally at least 95% homology, optionally at least 99% homology, optionally being identical to SEQ ID NO: 4.

21. The primer set of any of embodiment 16-20, further comprising a primer at least 80% homology, optionally at least 85% homology, optionally at least 90% homology, optionally at least 95% homology, optionally at least 99% homology, optionally being the primer of SEQ ID NO: 5.

22. A primer set comprising a primer selected from the group consisting of a primer at least 80% homology, optionally at least 85% homology, optionally at least 90% homology, optionally at least 95% homology, optionally at least 99% homology, optionally being the primer of SEQ ID NO: 9, a primer having at least 80% homology, optionally at least 85% homology, optionally at least 90% homology, optionally at least 95% homology, optionally at least 99% homology, optionally being the primer of SEQ ID: 12, or both a primer having at least 80% homology to SEQ ID NO: 9 and primer having at least 80% homology, optionally at least 85% homology, optionally at least 90% homology, optionally at least 95% homology, optionally at least 99% homology, optionally being the primer of SEQ ID NO: 12.

23. The primer set of embodiments 16-22, further comprising a primer having at 1 least 80% homology, optionally at least 85% homology, optionally at least 90% homology, optionally at least 95% homology, optionally at least 99% homology, optionally being the primer of SEQ ID NO: 7.

24. The primer set of any of embodiments 16-23, further comprising a primer having at least 80% homology, optionally at least 85% homology, optionally at least 90% homology, optionally at least 95% homology, optionally at least 99% homology, optionally being the primer of SEQ ID NO: 8.

25. The primer set of any of embodiments 16-24, further comprising a primer having at least 80% homology, optionally at least 85% homology, optionally at least 90% homology, optionally at least 95% homology, optionally at least 99% homology, optionally being the primer of SEQ ID NO: 10.

26. The primer set of any of embodiments 16-25, further comprising a primer having at least 80% homology, optionally at least 85% homology, optionally at least 90% homology, optionally at least 95% homology, optionally at least 99% homology, optionally being the primer of SEQ ID NO: 11.

27. A lyophilized pellet or powder comprising a primer set of any of the preceding claims.

28. A method of amplifying target DNA comprising exposing the target DNA to a primer set of any of the preceding claims under conditions that are suitable for amplification of the target DNA.

29. The method of embodiment 28, wherein the conditions include a temperature of 50° C. to 70° C.

30. The method of any of embodiments 28-29, further comprising detecting the presence of amplified target DNA.

EXAMPLES

DNA oligonucleotide sequences were prepared by Integrated DNA Technologies Company (IDT, Coralville, IA).

*Escherichia coli* strains TW04257, TW08039, TW07991, TW07931, TW07947, and TW07614 were obtained from the STEC Center at Michigan State University, East Lansing, MI.

*Escherichia coli* strains 0.1481 and 10.2360 were obtained from the *E. coli* Reference Center at Pennsylvania State University, University Park, PA.

*Escherichia coli* strains 045-2, 0121-1, 10000, SJ7, 96-0112, 96-1415, SJ9, and 07865 were obtained from the USDA Agricultural Research Service (USDA ARS), Wyndmoor, PA.

*Bacillus cereus* (ATCC 10876), *Enterobacter cloacae* (ATCC 13047), *Listeria ivanovii* (ATCC 19119), *Proteus vulgaris* (ATCC 13315), and *Salmonella* Newport (ATCC 6962) were obtained from the American Type Culture Collection (ATCC), Manassas, VA.

Pure cultures were propagated by streaking a frozen culture onto a tryptic soy agar plate and incubating the plate for 24 hours at 37° C. Colonies were suspended in 10 mL of buffered peptone water ISO broth (BPW-ISO, obtained from the 3M Company, St. Paul, MN) with a 10 microliter inoculation loop. Cultures were grown for 18 hours at 37° C. and were visibly turbid after incubation.

Example 1

Each prepared culture was diluted to a concentration of $1 \times 10^6$ colony forming units/mL (cfu/mL) in buffered peptone water ISO broth. A single diluted culture sample (20 microliters) was added to a lysis tube from a 3M Molecular Detection Assay 2-Cronobacter kit (catalog number MDA2CR096, obtained from the 3M Company). The lysis tube from the kit was supplied by the manufacturer pre-filled with a lysis solution. Each lysis tube was heated in a heat block (set at 100° C.) for 15 minutes and then cooled at ambient temperature for 5 minutes. A 20 microliter aliquot from the lysis tube was added to a reagent tube from the 3M Molecular Detection Assay 2-Cronobacter kit. Each reagent tube from the kit contained a LAMP+BART reagent pellet supplied by the manufacturer.

An aqueous mixture (2 microliters) containing six stx1 primers (SEQ ID NOS: 1-6) and $MgSO_4$ was added to each reagent tube and the sample was mixed using a micropipette. The resulting concentration of $MgSO_4$ in the reagent tube was 0.4 millimolar. The resulting concentrations of stx1 primers in the reagent tube were SEQ ID NO: 1 (0.2 micromolar), SEQ ID NO: 2 (0.4 micromolar), SEQ ID NO: 3 (0.8 micromolar), SEQ ID 4 (0.2 micromolar), SEQ ID NO: 5 (0.4 micromolar), SEQ ID NO: 6 (0.8 micromolar).

Each reagent tube was then placed in a 3M Molecular Detection System (MDS) Instrument (obtained from the 3M Company) and the instrument was operated according to the manufacturer's instructions. Bioluminescence (i.e. the BART reaction) was measured for 60 minutes at 60° C. Each tube was analyzed for pathogen detection according to the manufacturer's instructions. The time to obtain a positive result was recorded.

Comparative Example 1

As a comparative method, each culture sample was independently analyzed according to a Real-Time PCR assay method using primer and probe sequences described in Appendix 4 of the United States Department of Agriculture Foods Safety and Inspection Service Microbiology Laboratory Guidebook Method 5C.00. Each reaction had 12.5 uL of Agilent Brilliant III Ultra-Fast Master Mix (Catalog: 600880), 1.25 uM concentration forward stx primer, 1.25 uM concentration reverse stx primer and 0.25 uM of probe stx1, deionized water and 5 uL of sample for a total volume of 25 uL per reaction. Samples were run at one cycle at 95° C. for 10 minutes followed by 45 cycles of 95° C. for 15 seconds and 59° C. for 1 minute.

The specific sequences for primers and probes for Real Time PCR were as follows: Brilliant III Ultra-Fast Master Mix: Agilent (Catalog #600880); Stx F (Forward primer) 5' TTT GTY ACT GTS ACA GCW GAA GCY TTA CG 3'; Stx R (Reverse primer) 5' CCC CAG TTC ARW GTR AGR TCM ACD TC 3'; Stx1 Probe 5' 56-FAM-CTG GAT GAT/zen/CTC AGT GGG CGT TCT TAT GTA A-3IABkFQ 3'

The results of Example 1 and Comparative Example 1 are reported in Table 1.

Detection Assay 2-Cronobacter kit (catalog number MDA2CR096, obtained from the 3M Company). The lysis tube from the kit was supplied by the manufacturer pre-filled with a lysis solution. Each lysis tube was heated in a heat block (set at 1000 C) for 15 minutes and then cooled at ambient temperature for 5 minutes. A 20 microliter aliquot from the lysis tube was added to a reagent tube from the 3M Molecular Detection Assay 2-Cronobacter kit. Each reagent tube from the kit contained a LAMP+BART reagent pellet supplied by the manufacturer.

An aqueous mixture (2 microliters) containing stx2 primers (SEQ ID NOS: 7-12) and $MgSO_4$ was added to each reagent tube and the sample was mixed using a micropipette. The resulting concentration of $MgSO_4$ in the reagent tube was 0.4 millimolar. The resulting concentrations of stx2 primers in the reagent tube were SEQ ID NO: 7 (0.2 micromolar), SEQ ID NO: 8 (0.4 micromolar), SEQ ID NO: 9 (0.8 micromolar), SEQ ID NO: 10 (0.2 micromolar), SEQ ID NO: 11 (0.4 micromolar), SEQ ID NO: 12 (0.8 micromolar).

Each reagent tube was then placed in a 3M Molecular Detection System (MDS) Instrument (obtained from the 3M Company) and the instrument was operated according to the manufacturer's instructions. Bioluminescence (i.e. the BART reaction) was measured for 60 minutes at 60° C. Each culture sample was tested in triplicate (n=3) and analyzed for pathogen detection according to the manufacturer's instructions. The average time to obtain a positive result was recorded.

Comparative Example 2

As a comparative method, each culture sample was independently analyzed according to a Real-Time PCR assay

TABLE 1

Detection using primers for stx1

| Microorganism | Strain I.D. | stx1 Detected in Comparative Example 1 | stx1 Detected in Example 1 | Time to a Positive Result for Example 1 (minutes) |
| --- | --- | --- | --- | --- |
| Escherichia coli | 045-2 | yes | yes | 20.25 |
| Escherichia coli | TW04257 | yes | yes | 19.75 |
| Escherichia coli | TW07991 | yes | yes | 22 |
| Escherichia coli | 96-3285 | yes | yes | 20.5 |
| Escherichia coli | 0.1481 | yes | yes | 21 |
| Escherichia coli | 10000 | yes | yes | 19.25 |
| Escherichia coli | SJ7 | yes | yes | 19.75 |
| Escherichia coli | 96-0112 | yes | yes | 20.25 |
| Escherichia coli | 96-1415 | yes | yes | 20.5 |
| Escherichia coli | TW07947 | yes | yes | 21 |
| Escherichia coli | 10.2360 | yes | yes | 20.25 |
| Escherichia coli | TW08039 | no | no | n/a |
| Escherichia coli | TW07931 | no | no | n/a |
| Escherichia coli | 0121-1 | no | no | n/a |
| Bacillus cereus | 10876 | no | no | n/a |
| Enterobacter cloacae | 13047 | no | no | n/a |
| Listeria ivanovii | 19119 | no | no | n/a |
| Proteus vulgaris | 13315 | no | no | n/a |
| Salmonella Newport | 6962 | no | no | n/a |
| Escherichia coli | SJ9 | no | no | n/a |
| Escherichia coli | 07865 | no | no | n/a |
| Escherichia coli | TW07614 | no | no | n/a | n/a = not applicable (no positive result detected)

Example 2. Detection Using Primers for Stx2

Each prepared culture was diluted to a concentration of $1 \times 10^6$ colony forming units/ml, (cfu/mL) in buffered peptone water ISO broth. A single diluted culture sample (20 microliters) was added to a lysis tube from a 3M Molecular method using primer and probe sequences described in Appendix 4 of the United States Department of Agriculture Foods Safety and Inspection Service Microbiology Laboratory Guidebook Method 5C.00. Each reaction had 12.5 uL of Agilent Brilliant III Ultra-Fast Master Mix (Catalog: 600880), 1.25 uM concentration forward stx primer, 1.25 uM concentration reverse stx primer and 0.25 uM concentration of probe stx2, deionized water and 5 uL of sample for a total volume of 25 uL per reaction. Samples were run at one cycle at 95° C. for 10 minutes followed by 45 cycles of 95° C. for 15 seconds and 59° C. for 1 minute.

Specific sequences for primers and probes were as follows: Brilliant III Ultra-Fast Master Mix: Agilent (Catalog #600880); Stx F (Forward primer) 5' TTT GTY ACT GTS ACA GCW GAA GCY TTA CG 3'; Stx R (Reverse primer) 5' CCC CAG TTC ARW GTR AGR TCM ACD TC 3'; Stx2 Probe 5' 56-FAM-TCG TCA GGC/zen/ACT GTC TGA AAC TGC TCC-3IABkFQ 3.

The results of Example 2 and Comparative Example 2 are reported in Table 2.

TABLE 2

| | | Detection using primer set for stx2 | | |
|---|---|---|---|---|
| Microorganism | Strain I.D. | stx2 Detected in Comparative Example 2 | stx2 Detected by Example 2 | Time to a Positive Result Example 1 (minutes) |
| *Escherichia coli* | 045-2 | no | no | n/a |
| *Escherichia coli* | TW04257 | yes | yes | 16.25 |
| *Escherichia coli* | TW07991 | no | no | n/a |
| *Escherichia coli* | 96-3285 | no | no | n/a |
| *Escherichia coli* | 0.1481 | no | no | n/a |
| *Escherichia coli* | 10000 | no | no | n/a |
| *Escherichia coli* | SJ7 | no | no | n/a |
| *Escherichia coli* | 96-0112 | no | no | n/a |
| *Escherichia coli* | 96-1415 | no | no | n/a |
| *Escherichia coli* | TW07947 | no | no | n/a |
| *Escherichia coli* | 10.2360 | no | no | n/a |
| *Escherichia coli* | TW08039 | yes | yes | 16.5 |
| *Escherichia coli* | TW07931 | yes | yes | 17.5 |
| *Escherichia coli* | 0121-1 | yes | yes | 19.25 |
| *Bacillus cereus* | 10876 | no | no | n/a |
| *Enterobacter cloacae* | 13047 | no | no | n/a |
| *Listeria ivanovii* | 19119 | no | no | n/a |
| *Proteus vulgaris* | 13315 | no | no | n/a |
| *Salmonella* Newport | 6962 | no | no | n/a |
| *Escherichia coli* | SJ9 | yes | yes | 29.25 |
| *Escherichia coli* | 07865 | yes | yes | 21.75 |
| *Escherichia coli* | TW07614 | yes | yes | 20.5 | n/a = not applicable (no positive result detected)

What is claimed is:

1. A primer set comprising a primer having at least 80% homology to SEQ ID NO: 3; or
   a primer having at least 80% homology to SEQ ID NO: 6, or a combination of the foregoing primers.

2. A primer set of claim 1, comprising a primer having at least 80% homology to SEQ ID NO: 3 and primer having at least 80% homology to SEQ ID NO: 1.

3. The primer set of claim 1, further comprising a primer having at least 80% homology to SEQ ID NO. 2.

4. The primer set of claim 1, further comprising a primer having at least 80% homology to SEQ ID NO. 4.

5. The primer set of claim 1, further comprising a primer having at least 80% homology to SEQ ID NO: 5.

6. The primer set of claim 1, further comprising a primer at least 80% homology to SEQ ID NO: 3; and
   a primer at least 80% homology to SEQ ID NO: 6.

7. A lyophilized pellet or powder comprising a primer set of claim 1.

8. A method of amplifying target DNA comprising exposing the target DNA to a primer set of claim 1 under conditions that are suitable for amplification of the target DNA.

9. A primer set of claim 1, further comprising a primer having at least an 80% homology to SEQ ID 9 or a primer having at least an 80% homology to SEQ ID 12, or both.

10. A primer set of claim 9, further comprising a primer having at least an 80% homology to SEQ ID 7, a primer having at least an 80% homology to SEQ ID 10, a primer having at least an 80% homology to SEQ ID 8, a primer having at least 80% homology to SEQ ID 11, or more than one of the foregoing.

11. A primer set of claim 9, comprising a primer having at least 80% homology to SEQ ID 9 and a primer having at least 80% homology to SEQ ID 12.

12. A primer set of claim 11, further comprising a primer having at least 80% homology to SEQ ID 7, a primer having at least 80% homology to SEQ ID 10, or both.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Escherichia coli

<400> SEQUENCE: 1
ggttacattg tctggtgaca                                              20

<210> SEQ ID NO 2
<211> LENGTH: 17
<212> TYPE: DNA
<213> ORGANISM: Escherichia coli

<400> SEQUENCE: 2
cgactgatcc ctgcaac                                                 17

<210> SEQ ID NO 3
<211> LENGTH: 42
<212> TYPE: DNA
<213> ORGANISM: artificial
<220> FEATURE:
<223> OTHER INFORMATION: synthetic

<400> SEQUENCE: 3
gaatggcgat ttatctgcat cgtagctata ccacgttaca gc                     42

```
<210> SEQ ID NO 4
<211> LENGTH: 21
<212> TYPE: DNA
<213> ORGANISM: Escherichia coli

<400> SEQUENCE: 4
tcacagttac aaaccgtaac a                                          21

<210> SEQ ID NO 5
<211> LENGTH: 20
<212> TYPE: DNA
<213> ORGANISM: Escherichia coli

<400> SEQUENCE: 5
catagtggaa cctcactgac                                            20

<210> SEQ ID NO 6
<211> LENGTH: 43
<212> TYPE: DNA
<213> ORGANISM: artificial
<220> FEATURE:
<223> OTHER INFORMATION: synthetic

<400> SEQUENCE: 6
ctacttctta tctggattta atgtcgctct tgccacagac tgc                  43

<210> SEQ ID NO 7
<211> LENGTH: 17
<212> TYPE: DNA
<213> ORGANISM: Escherichia coli

<400> SEQUENCE: 7
gaacgttccg gaatgca                                               17

<210> SEQ ID NO 8
<211> LENGTH: 21
<212> TYPE: DNA
<213> ORGANISM: Escherichia coli

<400> SEQUENCE: 8
taccactgaa ctccattaac g                                          21

<210> SEQ ID NO 9
<211> LENGTH: 41
<212> TYPE: DNA
<213> ORGANISM: artificial
<220> FEATURE:
<223> OTHER INFORMATION: synthetic

<400> SEQUENCE: 9
gatgcatctc tggtcattgt agtcactcac tggtttcatc a                    41

<210> SEQ ID NO 10
<211> LENGTH: 20
<212> TYPE: DNA
<213> ORGANISM: Escherichia coli

<400> SEQUENCE: 10
atacacagga gcagtttcag                                            20

<210> SEQ ID NO 11
<211> LENGTH: 17
<212> TYPE: DNA
<213> ORGANISM: Escherichia coli
```

```
<400> SEQUENCE: 11
gcagaagcct tacgctt                                                  17

<210> SEQ ID NO 12
<211> LENGTH: 40
<212> TYPE: DNA
<213> ORGANISM: artificial
<220> FEATURE:
<223> OTHER INFORMATION: synthetic

<400> SEQUENCE: 12
tctgcgtttt gtcactgtcc tgacgaaatt ctctctgtat                         40
```